(12) United States Patent
Pearce et al.

(10) Patent No.: US 11,103,614 B2
(45) Date of Patent: Aug. 31, 2021

(54) SKIN COMPATIBLE COMPOSITION

(71) Applicant: Trio Healthcare Ltd, Skipton (GB)

(72) Inventors: Lloyd Pearce, Skipton (GB); Stewart Lee, Skipton (GB)

(73) Assignee: TRIO HEALTHCARE LIMITED, Skipton (GB)

( * ) Notice: Subject to any disclaimer, the term of this patent is extended or adjusted under 35 U.S.C. 154(b) by 182 days.

(21) Appl. No.: 16/085,399

(22) PCT Filed: Mar. 14, 2017

(86) PCT No.: PCT/GB2017/050690
§ 371 (c)(1),
(2) Date: Sep. 14, 2018

(87) PCT Pub. No.: WO2017/158340
PCT Pub. Date: Sep. 21, 2017

(65) Prior Publication Data
US 2019/0083677 A1 Mar. 21, 2019

(30) Foreign Application Priority Data

Mar. 14, 2016 (GB) .................................... 1604308
Feb. 24, 2017 (GB) .................................... 1703038

(51) Int. Cl.
*A61L 24/00* (2006.01)
*C08K 5/56* (2006.01)
*C08L 33/02* (2006.01)
*C08L 83/04* (2006.01)

(52) U.S. Cl.
CPC ....... *A61L 24/0094* (2013.01); *A61L 24/0031* (2013.01); *A61L 24/0073* (2013.01); *A61L 2400/14* (2013.01); *C08K 5/56* (2013.01); *C08L 33/02* (2013.01); *C08L 83/04* (2013.01); *C08L 2203/02* (2013.01)

(58) Field of Classification Search
CPC ............. A61L 24/0094; A61L 24/0031; A61L 24/0073; C08K 5/56; C08L 33/02; C08L 83/04
See application file for complete search history.

(56) References Cited

U.S. PATENT DOCUMENTS

| 4,231,369 A | 11/1980 | Sorensen et al. |
| 4,846,798 A | 7/1989 | Holtermann |
| 6,471,985 B2 | 10/2002 | Guyuron et al. |
| 7,842,752 B2 | 11/2010 | Bougherara |
| 8,124,675 B2 | 2/2012 | Bougherara |
| 8,436,121 B2 | 5/2013 | Lam et al. |
| 8,545,468 B2 | 10/2013 | Fabo et al. |
| 2003/0190301 A1 | 10/2003 | Fry |
| 2004/0102744 A1 | 5/2004 | Fattman |
| 2006/0228318 A1 | 10/2006 | Fabo |
| 2007/0020319 A1 | 1/2007 | Bougherara |
| 2007/0202245 A1* | 8/2007 | Gantner .................. A61L 15/58 427/2.1 |
| 2009/0306571 A1* | 12/2009 | Lam ........................ A61L 24/08 602/56 |
| 2012/0149810 A1 | 6/2012 | Bougherara |

FOREIGN PATENT DOCUMENTS

| EP | 0334489 | 9/1989 | |
| EP | 0687166 | 8/1998 | |
| GB | 2274650 | 8/1994 | |
| GB | 2518468 | 3/2015 | |
| GB | 2527873 | 6/2015 | |
| GB | 2527873 | 7/2018 | |
| JP | 59-104314 A | 6/1984 | |
| JP | 05-503863 A | 6/1993 | |
| JP | 2007-532179 A | 11/2007 | |
| JP | 2009-536228 A | 10/2009 | |
| JP | 2011-72437 A | 4/2011 | |
| JP | 2014-505117 A | 2/2014 | |
| WO | 93/18725 | 9/1993 | |
| WO | 02066087 | 8/2002 | |
| WO | 2005/102403 | 11/2005 | |
| WO | WO-2005102403 A1 * | 11/2005 | ............. A61L 15/58 |
| WO | 2007/059775 | 5/2007 | |
| WO | 2007/128320 | 11/2007 | |
| WO | 2008/074333 | 6/2008 | |
| WO | 2013/030580 | 3/2013 | |
| WO | 2013/033131 | 3/2013 | |
| WO | 2015/082877 A1 | 6/2015 | |
| WO | 2016/123366 A1 | 8/2016 | |

OTHER PUBLICATIONS

International Search Report and Written Opinion, International Patent Application No. PCT/GB2017/050690, dated May 31, 2017 (11 pages).
Combined Search and Examination Report, GB Patent Application No. GB1604308.5, dated Nov. 30, 2016 (6 pages).

\* cited by examiner

*Primary Examiner* — Edward J Cain
(74) *Attorney, Agent, or Firm* — Hamre, Schumann, Mueller & Larson, P.C.

(57) ABSTRACT

A skin compatible component attachable to mammalian skin. The component is formed as a silicone matrix comprising a polyorganosiloxane derived silicone polymer and moisture control particulate distributed within the polymer network being configured to absorb moisture from the skin. The skin compatible component may be utilised as an ostomy wafer or flange to secure an ostomy appliance to the skin and in particular peri-skin.

31 Claims, 3 Drawing Sheets

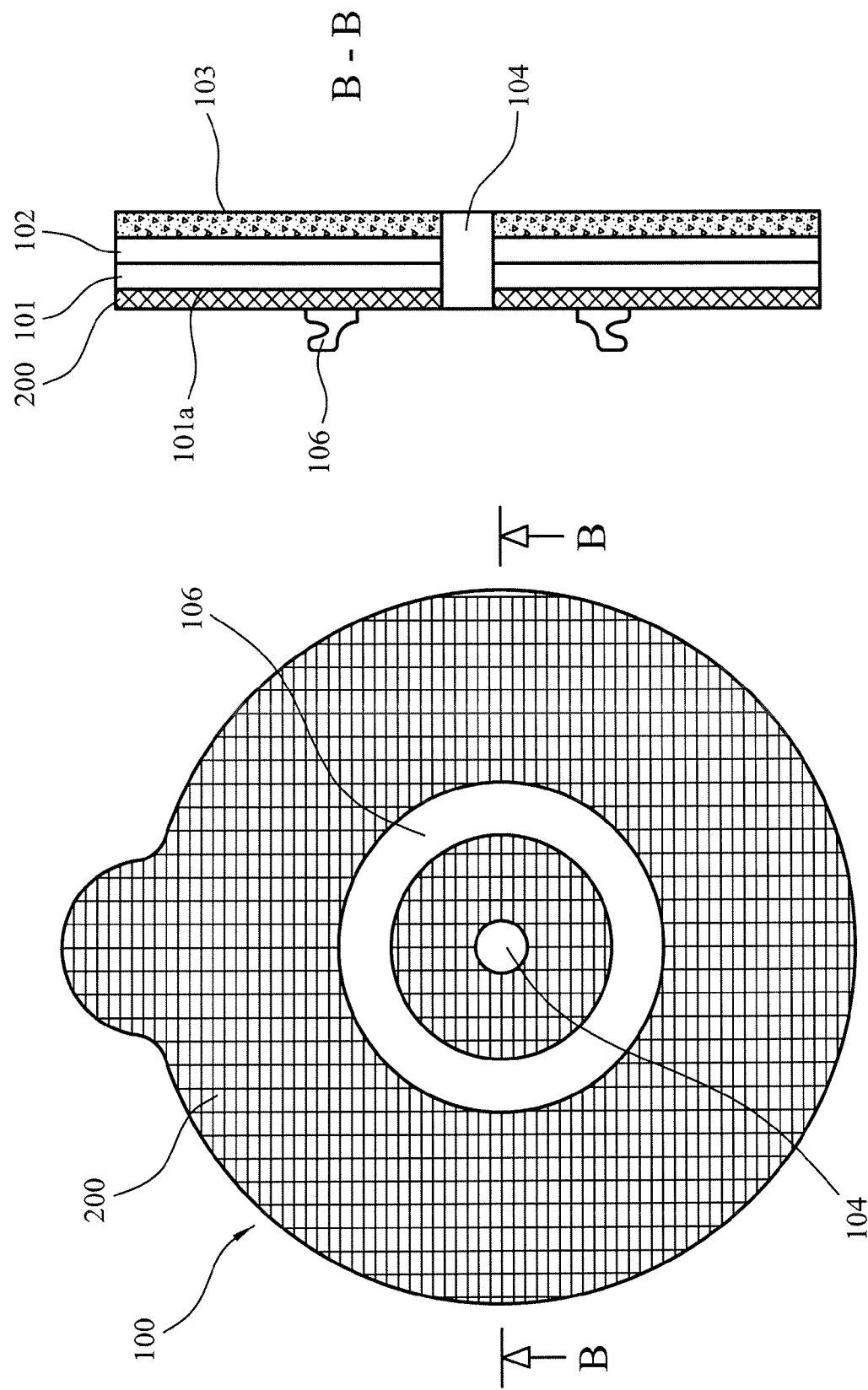

SKIN COMPATIBLE COMPOSITION

FIELD OF INVENTION

The present invention relates to an adhesive skin compatible composition and in particular, although not exclusively, to a skin adhesive component suitable for coupling an ostomy appliance to the peristomal skin region of an ostomate.

BACKGROUND ART

An ostomate having a colostomy, ileostomy or urostomy requires a collection receptacle, such as a bag, be secured around the stoma being an artificial opening exiting through a person's abdomen. Typically, the collection bag is secured to the peristomal skin by means of an adhesive disc that may be required to be changed several times daily. As frequent removal of the adhesive disc causes irritation and damage to the skin, ostomy couplings have been developed in an attempt to increase comfort and improve wellbeing. Ostomy coupling arrangements commonly referred to as 'two-piece' systems comprise a first coupling part fitted with a ostomy bag to receive stoma discharge and a second coupling part (releasably connectable with the first) provided on a base layer (or wafer) that may be adhered to the peristomal skin. Accordingly, the ostomy bag may be changed readily without having to detach the base layer from the skin. Many different types of coupling arrangements have been proposed to maximise seal strength and minimise undesirable discharge. Example two-piece ostomy bag systems are described in EP 0687166; EP 1959881; U.S. Pat. No. 4,846,798; WO 93/18725 and EP 0334489.

However, as a person is required to wear an ostomy coupling continuously, both two-piece and one-piece coupling arrangements must be completely interchanged at regular periods due to moisture uptake when in contact with the skin that cause erosion and breakdown of the adhesive disc. As will be appreciated, degradation of the coupling wafer will compromise the sealing contact with the skin and hence is very undesirable. Conventionally, the adhesive discs of ostomy appliances comprise hydrocolloids that possess high absorption capacity and are generally benign when in contact with the skin for long periods. However, conventional discs are disadvantageous due to their erosion and breakdown with moisture uptake. Additionally, such systems fail to provide a correct balance of the demands for a secure seal to be maintained around the stoma during attachment whilst allowing the coupling to be detached readily without causing skin irritation. Given the regularity with which even two-piece arrangement require changing, the compromise between adhesion and release is not found via such conventional systems. Accordingly, what is required is a coupling component or arrangement contactable with the skin that facilitates patient security and comfort and maximises wear time.

SUMMARY OF THE INVENTION

It is an objective of the present invention to provide an adhesive skin contactable component and in particular, although not exclusively, an ostomy coupling component or arrangement configured to exhibit enhanced moisture management when mounted in position at the peristomal skin. It is a specific objective to provide a skin attachable component being in particular an ostomy appliance adhesive disc that is resistant to erosion and breakdown in response to moisture so as to extend patient wear time.

The objectives are achieved, by providing a biocompatible silicone based layer, disc or pad positionable in contact with the skin, peri-skin and/or peristomal skin that comprises moisture management characteristics including moisture absorption and breathability. In particular the objectives are achieved via a silicone adhesive layer being a room temperature vulcanisation silicone (RTV silicone) formed from a catalytic, addition cured, two-part system.

The objectives are further achieved specifically via a synthetic silicone gel based adhesive layer formed from a polyorganosiloxane derived silicone polymer network comprising Si—O and Si—C bonds in which a moisture control particulate is distributed within the Si network. The present polyorganosiloxane derived material incorporating the superabsorbent (moisture absorbing) particulate exhibits the desired flexibility and appropriate free internal volume to achieve the desired water vapour transmission rate (WVTR) from the skin and through the matrix and also to accommodate the superabsorbent particulate. Such moisture management, including breathability, provides an ostomy wafer or gasket that may be worn comfortably by an ostomate for significantly longer time periods than is currently available for conventional systems. The moisture control additive, in the form of particulates, is selected to achieve the desired substrate adhesion at the skin with low or very low risk of maceration. The synergistic behaviour of the silicone polymer and absorbent particulate provides the desired balance between moisture absorption into the silicone matrix without being detrimental to adhesion and the cohesive properties of the wafer. The present base layer is particularly adapted to provide optimised transmission of moisture vapour through the main body and across the full surface area of contact between the wafer and the skin. The present hydrophilic silicone based wafer accordingly maintains its shape profile, does not erode in the presence of moisture and is gas, vapour and moisture permeable.

The term 'particulate' used herein encompasses polymer species having a micron or submicron size suitable for dispersion within a larger polymer network, gel phase and in particular a silicone polymer network (adapted or suitable to accommodate a superabsorbent particulate (SAP)). The moisture control SAP may be a hydrocolloid including a naturally occurring semi-synthetic or synthetic hydrocolloid.

Naturally-occurring hydrocolloids suitable for use with the subject invention include polysaccharides and cellulosic materials. Example polysaccharide hydrocolloids may comprise plant extracts including gums including in particular xanthan gum or pectin. Example cellulosic materials may comprise cellulose; carboxymethyl cellulose; carboxymethyl β-glucan; cross-linked sodium carboxymethyl cellulose; sodium carboxymethyl cellulose; methylcellulose; hydroxyethylcellulose and hydroxypropyl cellulose.

Semi-synthetic hydrocolloids may comprise starch or cellulose, such as starch-acrylonitrile graft copolymer; a starch polyacrylate salt, and sulfuric acid, vinyl sulfonate, methacrylic acid, vinyl alcohol, vinyl chloride copolymers; guar gums, esterified uronic acid containing polymers such as hyaluronates and alginates, hyaluronate polyvinyl alcohol blends; chitosans formed from partial or complete deacetylation of chitin and/or depolymerisation.

Synthetic hydrocolloids suitable for use with the subject invention may comprise polyvinyl pyrrolidone; carboxyvinyl polymers and polyethylene oxide polymers; polymers of methyl vinyl ether and maleic acid and derivatives; polyvinyl alcohol, high molecular weight polyethylene glycols and polypropylene glycols; or polyethylene oxides.

Preferably, the moisture control SAP comprises sodium polyacrylate. Such a particulate has been found to be compatible with the as-formed addition cured silicone matrix and to absorb moisture released form the skin so as to swell appropriately without destroying the cohesive strength of the matrix hence the skin layer covering. Additionally, a sodium polyacrylate SAP contributes to providing the desired WVTR across the adhesive layer and facilitates the desired wicking action. In particular preferred sodium polyacrylate particulates have excellent water absorption property of the order of 350 g/g $H_2O$ and 55 g/g 0.9% NaCl. Additionally, such particulates be may configured with a 'fine' particle size selected such that a surface area/volume ratio is optimised to maximise the rate of moisture absorption. By way of example, a spherical sodium polycrylate SAP having a nominal radius of 20 μm has a surface area to volume ratio five times that of an alternative non-sodium polyacrylate particle of nominal radius of 100 μm. Additionally, sodium polyacrylate comprises a pH 6-7 and therefore specific/additional neutralisation is not required.

According to a first aspect of the present invention there is provided a skin compatible component attachable to mammalian skin comprising: a silicone polymer network derived from the addition curing of a first part including a vinyl functionalised siloxane polymer and a second part including a silicon hydride (Si—H) containing crosslinker, in the presence of a metal catalyst; and a superabsorbent particulate distributed within the polymer network configured to absorb moisture from the skin; wherein the superabsorbent particulate has an average particle size less than 150 μm.

Preferably, the peel adhesion of the present component under standard test conditions according to standard ISO 29862 (standard LTM-01: Self-adhesive tapes—Determination of peel adhesion properties—180 Degree Peel from Stainless Steel Plate at a constant rate extension of 300 mm/min) is in a range 0.2 to 3.0 N/25 mm, 0.5 to 3.0 N/25 0.8 to 3.0 N/25 mm, 1.5 to 3.0 N/25 mm, 1.8 to 3.0 N/25 mm, 2.0 to 3.0 N/25 mm or 2.0 to 2.5 N/25 mm.

In particular, the present silicone adhesive component when incorporated as part of a multicomponent laminate assembly according to the subject invention preferably comprises a peel adhesion, according to ISO 29862 (25 mm strip stainless steel substrate) of 0.2 to 0.8 N or 0.4 to 0.6 N. This is to be contrasted with conventional hydrocolloid skin contactable components that typically comprise a higher peel adhesion of the order of 6 to 9 N (ISO 29862).

Preferably, a component according to the subject invention comprises an adhesive tack in a range 2 to 12 N, 2 to 10 N, 3 to 10 N, 4 to 10 N, 5 to 10 N, 6 to 10 N or 6 to 8 N according to (standard LTM-013: Adhesive tack test—force required to pull a 12 mm diameter stainless steel compression plate at 90° angle from the surface of an adhesive at a constant rate extension of 50 mm/minute).

The present skin compatible component via the polyorganosiloxane derived silicone polymer exhibits high elasticity and low shear strength. The elastic nature of the present silicone adhesive layer provides a coupling assembly configured to retain its shape when stretched below its break point when allowed to relax. The present silicone based components is formed as a silicone gel adhesive composition that also provides a balance of elastic and viscoelastic properties so as to achieve good adhesion of medical appliances to the skin whilst being readily peelable or removable from the skin when desired. Due to the moisture absorption and the moisture vapour transmission rate across the silicone layer, the subject invention provides a device, coupling or appliance attachable to the skin that maintains and promotes skin health. The selection of the particulate described herein and silicone polymer act together to achieve the desired chemical, physical and mechanical properties so as to provide a skin compatible component that does not degrade, erode or breakdown with the uptake of moisture. Accordingly, a skin contactable coupling is provided with considerably longer skin wear times relative to conventional devices.

The vulcanised silicone polymer is obtained by reacting an alkenyl-substituted polydiorganosiloxane, preferably a polydimethylsiloxane having silicon-bonded vinyl, allyl or hexenyl groups, and an organosiloxane containing silicon-bonded hydrogen atom and a catalyst for the reaction of the SiH groups with the Si-alkenyl (SiVi) groups, such as a platinum metal or its compounds or its complexes thereof. The ratio of SiVi:SiH can be 10:1 to 1:10. Preferred ratio of SiVi:SiH is 1:1. Altering the ratio of the reacting silicones from 1:1 ratio can change the adhesive properties of the layer. If a firmer, lower tack gel is required, the SiH component is higher than SiVi, and if a softer layer with higher tack is required, the SiVi component may be higher than SiH. The silicone compositions may be cured at ambient temperatures, but curing times can be reduced by exposure to elevated temperatures, from about 40° C. to about 150° C. Non-limiting examples of such silicone polymer precursors include Soft Skin Adhesives SSA MG-7-1010, SSA 7-9900, 7-9950 from Dow Corning Corporation, Silpuran® 2114, 2117, 2122, 2130, 2140, 2142 and combinations thereof, SilGel® 612 from Wacker Chemicals. Hydrophilic group containing silicones, according to the present disclosure, may contain polar groups such as acid, amido, amino, sulfonyl, carboxyl, phosphate, phosphonate, etc., on the polydimethylsiloxane backbone. These groups could be present in an ionic form.

The moisture control particulate having an average particle size of less than 150 μm provides a 'fine' particle distribution within the polymer network. This is advantageous to provide the moisture management characteristic of the subject invention and in particular to achieve a capillary action moisture transport through the silicone polymer layer such that moisture (water) is readily transported across the silicone polymer layer. Accordingly, the present silicone polymer via the desired particle size of the moisture control particulate is configured to absorb and release moisture when in contact with the skin as the skin compatible component is worn by a patient for example at the peristomal skin. As will be appreciated, the surface area to volume ratio is an important factor in determining the active surface area for absorption of moisture from the skin in that for any given shape of particle, the surface area to volume ratio is inversely proportional to particle size. The present particulate size when incorporated within a polyorganosiloxane derived silicone matrix has been found to act synergistically to achieve the desired performance of the skin compatible component with regard to adhesion, release, absorption and moisture vapour transmission rate. This is achieved in part as the resulting network, formed from the vulcanisation of the two-part system, comprises the desired cross linkage density and open micro-structure that entraps the particulate whilst allowing the particulate to swell in use without destroying the cohesiveness of the silicone layer covering.

A skin compatible component according to the subject invention comprises an optimised water vapour transmission rate so as to provide a component configured to balance transepidermal water loss (TEWL) from the skin with the water vapour transmission rates of the skin compatible component (covering the skin). This is achieved in part by the sodium polyacrylate SAP as detailed herein having the preferred particle size and at the preferred concentration within the mix. According to one aspect, the water vapour transmission rate (WVTR) of the present component may be in a range 100 to 500 g/m$^2$·24 h; 150 to 400 g/m$^2$·24 h; 200 to 300 g/m$^2$·24 h or 220 to 280 g/m$^2$·24 h using an upright cup method with a layer thickness of 635 µm to 750 µm. Such water vapour transmission rates may be correlated with a layer thickness of the silicone adhesive component having a thickness of 250 µm to 1,000 µm; 500 µm to 1,000 µm; or 635 µm to 1,000 µm.

The silicone part of the network formed from the addition curing of a first part and a second part is advantageous to provide the desired physical and mechanical properties of the resulting cured component. In particular, via the choice of the first and second part components the degree of crosslinking may be controlled so as to provide the desired network micro-structure to appropriately entrap the superabsorbent moisture control SAP as immobilised particles within the network. Additionally, the two-part addition cured composition provides the desired viscoelastic properties, adhesive tack, adhesive peel, moisture absorption, cohesive strength and WVTR. As will be appreciated, at least some of these characteristics may be considered contrary with regard to the attachment to mammalian skin and the present component and method of manufacture provides a balance of these considerations so as to optimise the component for moisture management at the skin.

Accordingly, the present component exhibits enhanced wear times relative to conventional hydrocolloid based components whilst providing the desired adhesion (adhesive tack) and adhesive peel so as to avoid problems of skin maceration and 'stripping' on release. Additionally, the cohesive strength of the component is optimised via the two-part addition curing adhesive so as to maintain the integrity of the adhesive skin covering in response to moisture absorption/swelling of the skin covering for extended continuous wear times in excess of 70 hours and up to or beyond 400 hours. In particular, the two-part addition cured component provides a desired WVTR that is configured specifically to complement the skin TEWL. In particular, the present two-part addition cured system may be considered advantageous over conventional one-part pressure sensitive adhesives (PSAs) that do not comprise the same crosslinking density and cohesive strength.

Preferably, the superabsorbent particulate comprises an average particle size in the range 10 to 40 µm, 15 to 35 µm or 20 to 30 µm. Preferably, the superabsorbent particulate is distributed within the polymer network at a concentration in the range 5 to 45 wt %, 10 to 40 wt %, 15 to 35 wt % or 20 to 30 wt %. The particle size according to the subject invention is advantageous to achieve the desired rate and speed of moisture absorption from the skin. Additionally, such a configuration provides the required rate of moisture transmission across the adhesive layer due to wicking. In particular, a volume of moisture absorbed from the skin is appropriately transported across the silicone adhesive layer (and away from the skin) to avoid skin maceration, undesirable moisture welling and hence lifting/peeling of the silicone layer in use. The particle size also provides homogeneity and uniform distribution of the superabsorbent particulate (SAP) within the silicone matrix that enhances the cohesive strength. In one aspect, the superabsorbent SAP and preferably the sodium polyacrylate (SAP) may comprise an absorption of 350 g·g$^{-1}$ (deionised water) or 55 g·g$^{-1}$ (0.9 weight % by volume of saline solution).

Preferably, an organosilicone resin is included in the first or second part prior to addition curing. Preferably, the organosilicone resin is an MQ resin. The organosilicone resin and in particular the MQ resin is advantageous to provide the desired balance between adhesive tack and peel/release characteristics. Optionally, the MQ resin has at least one reactive group such as hydroxyl, alkoxy, hydride, or vinyl functionalities. The silicone resin may comprise a cage-like oligosiloxane with the general formula of $R_nSiX_mO_y$, where R is a non-reactive substituent, usually Me or Ph, and X is a functional group H, OH, vinyl, or OR. These groups are further condensed to enhance or contribute to the resulting crosslinked polysiloxane network. Non-limiting examples of commercially available MQ resins are MQ-RESIN POWDER 803 TF from Wacker Chemical Corporation; VQM-135, VQM-146, HQM-105, HQM-107, SQO-299, and SQD-255 from Gelest Inc., Prosil 9932, MQOH-7 from SiVance, LLC.

Preferably, a cohesive strengthening agent is including in the first part or the second part prior to addition curing. Optionally, the cohesive strengthening agent comprises any one or a combination of the set of: fumed silica, fumed alumina, colloidal silica, nanoclays, silicates, silane treated organic polymers, polymeric metal oxides, and non-polymeric metal oxides. Preferably, the cohesive strengthening agent comprises fumed silica. The strengthening agent contributes to the cohesive strength characteristics of the component and assists with maintaining integrity of the silicone adhesive layer in response to moisture absorption by the SAP. In particular, the cohesive strengthening agent is further advantageous to minimise and eliminate layer residue once released from the skin. The strengthening agent is further advantageous to facilitate distribution of the SAP within the matrix. Furthermore, the cohesive strengthening agent further improves the integrity and cohesive strength at the perimeter edge of the silicone layer so as to reduce 'edge bleed'. Non-limiting examples of cohesive strengthening agents of the present disclosure include silica, which could be fumed or precipitated silica such as AEROSIL® and SIPERNAT® grades, respectively, from Evonik Industries. The silica powders could be hydrophilic or hydrophobic, such as AEROSIL® 300, AEROSIL® 255, AEROSIL® R 812, AEROSIL® R 812 S, SIPERNAT® 120, SIPERNAT® 218, etc. Other non-limiting examples of cohesive strengthening agents include fumed alumina, colloidal silica, nanoclays, silicates, silane treated organic polymers, polymeric metal oxides, non-polymeric metal oxides, and the like.

The present skin compatible wafer component may be worn by a patient continuously for over 400 hours without edge lifting, wrinkles, ripples or other degradation of the silicone layer.

According to a second aspect of the present invention there is provided an ostomy coupling comprising: a moisture and gas permeable support layer; an ostomy appliance or ostomy appliance connection provided at a first surface of the support layer; and a skin compatible component as claimed herein attached to a second surface of the support layer.

Optionally, the polyurethane layer comprises a thickness in the range 0.02 to 0.08 mm. The polyurethane layer may comprise a moisture vapour transmission rate of 1200 g·m$^2$·24 h$^{-1}$ using an upright cup method; a tensile strength of 40 to 50 MPa and an elongation of 500%. Preferably, the support layer may be regarded as porous so as to allow transmission of moisture, water vapour and gas through the support layer and hence provide a fully 'breathable' skin adhesive covering pad or disc.

Preferably, the silicone matrix layer is protected by a release liner configured for quick and convenient removal prior to mounting of the silicone layer in direct contact with the skin. Optionally, the release liner may comprise a thermoformable material, a fluoropolymer treated film, LDPE, polyethylene terephthalate (PET) or a polycarbonate based material.

Optionally, the support layer comprises any one or a combination of the set of: a breathable silicone layer; a polyethylene block amide polymer; a polytetrafluoroethylene polymer; an acrylic latex polymer; or a polyolefin based layer. Preferably, the support layer comprises polyurethane.

Optionally, the ostomy appliance comprises a bag or pouch attached to the support layer directly or via an intermediate layer. Optionally, the intermediate layer may comprise polyethylene or may comprise any one or a combination of the set of: a polyester disc; a non-woven polyester; a non-woven polyethylene; a polypropylene disc; a non-woven polypropylene. Optionally, the intermediate layer may be a single or double sided adhesive annular ring capable of adhering to one or more components forming part of the assembly. Such a configuration would avoid a requirement to weld the intermediate layer to other components for example via RF or sonic welding.

Preferably, the ostomy appliance connection comprise a first part of a two-part bag or pouch connection assembly (as are known within the art) in which a second part of the connection assembly is mounted at a bag or pouch, the first part and the second part capable of releasable mating to detachably secure the bag or pouch to the coupling.

Optionally, the coupling comprises an opening extending through the support layer and the skin compatible component. Optionally, the ostomy appliance comprises a bag or pouch attached to the support layer directly or via an intermediate layer. Optionally, the intermediate layer comprises polyethylene. Optionally, the intermediate layer comprises any one or a combination of the set of: a polyester disc; a polyester gauze; a polyethylene gauze; a polypropylene disc; a polypropylene gauze. Such materials may be configured as single or doubled sided adhesive rings or pads capable of adhering to other components within the assembly.

Optionally, the ostomy appliance connection comprises a first part of a bag or pouch connection assembly in which a second part of the connection assembly is mounted at a bag or pouch, the first part and the second part capable of releasable mating to detachably secure the bag or pouch to the coupling.

To further enhance the moisture management and vapour transmission of the present coupling (and in turn avoid skin maceration and the like) the coupling may further comprise an additional skin contact layer positioned at the skin facing side of the skin compatible component. Preferably, the additional skin contact layer is a silicone based adhesive component extending over selected regions of a skin facing side or surface of the skin compatible component.

Preferably the additional skin contact layer is formed non-continuously over the skin compatible component so as to provide exposed areas of the skin compatible component that are devoid of the additional skin contact layer. Accordingly, with the material in contact with the skin, adhesion is provided firstly via the additional skin contact layer and secondly by the exposed surface area regions of the skin compatible component (not covered by the additional skin contact layer). Such a configuration improves the skin friendliness of the present material during use by enhancing the breathability of the silicone layer and allowing moisture to be readily removed from the skin without causing irritation.

Preferably, the additional skin contact layer is a silicone adhesive layer provided on the skin facing surface of the skin compatible component and intended to be positioned in contact with the skin to adhere to the skin, the additional skin contact layer being non-continuous over the skin facing surface of the skin compatible component such that areas of said surface are not concealed by the additional skin contact layer, said areas capable of positioning directly adjacent and/or in contact with the skin.

Optionally, the additional skin contact layer comprises a two-part catalysed, silicone elastomer. Optionally, the additional skin contact layer may comprise a composite of a plurality of different silicones and/or silicone based materials.

Optionally, the additional skin contact layer comprises the same material as the skin compatible component. Optionally, the additional skin contact layer comprises the same material as the skin compatible component but without the superabsorbent particulate. That is, the additional skin contact layer may comprise a silicone polymer network derived from the addition curing of a first part including a vinyl functionalised siloxane polymer and a second part including a silicon hydride containing crosslinker, in the presence of a metal catalyst.

Optionally, the additional skin contact layer may be formed as lines or dots on the skin facing surface of the skin compatible component. In such a configuration, the skin compatible component may be regarded as a substrate. Where the additional skin contact layer is formed as individual dots, flecks or marks, the pattern created by these dots may be uniform across the skin facing surface of the substrate. Alternatively, the pattern may change over the substrate surface and the material may comprise different patterns at different regions over the substrate. Where the additional skin contact layer comprises lines or ridges extending over the substrate, these lines may extend in different directions where the spacing between the lines or ridges is the same or variable across the substrate surface. Optionally, the lines may create a square, rectangular or circular grid pattern. Optionally, the lines or ridges are distributed at the skin facing surface to create geometric shapes. Preferably, the additional skin contact layer is bonded to the substrate and takes the form of concentric circles extending around a central aperture extending through the substrate and/or the multilayer coupling.

According to a third aspect of the present invention there is provided a method of manufacturing a skin compatible component attachable to mammalian skin comprising: mixing a first part including a vinyl functionalized siloxane polymer with a second part including a silicon hydride (Si—H) containing crosslinker to form a mix; incorporating within the mix a superabsorbent particulate having an average particle size of less than 150 µm; curing the mix via a metal catalyst; wherein the superabsorbent particulate is distributed within the resulting addition cured silicone polymer network.

Preferably, the first part or the second part further comprise an organosilicone resin. Preferably, the organosilicone resin comprises an MQ resin. Preferably, the organosilicone resin is a silicic acid, trimethylsilylester with silanol functionality. Preferably, the organosilicone resin is included in the mix at 0.2 to 1.8 wt %, 0.4 to 1.6 wt %, 0.6 to 1.4 wt % or 0.8 to 1.2 wt %.

Preferably, the first or second part further comprises a cohesive strengthening agent. Preferably, the cohesive strengthening agent comprises fumed silica. Preferably, the fumed silica comprises a bulk density of 0.4 to 0.8 g/mL and a Brunauer-Emmitt-Teller (BET) specific surface area of 200 to 320 $mm^2/g$, 210 to 310 $mm^2/g$, 230 to 300 $mm^2/g$ or 230 to 290 $mm^2/g$. Preferably, the fumed silica is included within the mix at 0.2 to 2.0 wt %, 0.3 to 2.0 wt %, 0.5 to 1.5 wt % or 0.8 to 1.2 wt %.

Preferably, the superabsorbent particulate and preferably the sodium polyacrylate particulate comprises a particle size in a range 10 to 40 µm, 15 to 35 µm or 20 to 30 µm. Preferably, the superabsorbent particulate and preferably the sodium polyacrylate particulate is included within the mix at 5 to 45 wt %, 15 to 35 wt %, 20 to 30 wt % or 22 to 28 wt %.

Preferably, the vinyl functionalized siloxane polymer comprises a vinyl-terminated polydimethylsiloxane (PDMS). Preferably, the silicon hydride (Si—H) containing crosslinker comprises a hydride-terminated polydimethylsiloxane (PDMS).

Preferably, the vinyl-terminated polydimethylsiloxane (PDMS) comprises a first vinyl-terminated PDMS having a mass average of 10,000 to 20,000 and a second vinyl-terminated PDMS having a mass average of 70, 000 to 100,000. These mass average polymer distributions provide a resulting cured silicone matrix with the desired crosslinking density, porosity and cohesive strength to withstand the swelling of the layer during use and not to degrade which would otherwise result in failure of the covering.

Preferably, the vinyl functionalized siloxane polymer comprises a vinyl-terminated polydimethylsiloxane (PDMS) and the silicon hydride (Si—H) containing crosslinker comprises a hydride-terminated polydimethylsiloxane (PDMS).

Preferably, the first part is included within the mix at 30 to 40 wt % or 31 to 35 wt % and the second part is included within the mix at 30 to 40 wt % or 33 to 37 wt %.

Preferably, the superabsorbent particulate is included within the mix at 20 to 30 wt % or 22 to 28 wt %. Preferably, an MQ resin included in the mix at 2 to 8 wt % or 3 to 7 wt %. Preferably, fumed silica included within the mix at 0.2 to 2.0 wt %, 0.5 to 1.5 wt % or 0.8 to 1.2 wt %.

Preferably, the first part further comprises an organoplatinum catalyst and a silicone-vinyl containing inhibitor and the second part further comprises a vinyl-terminated polydimethylsiloxane (PDMS) and preferrably the superabsorbant particulate is sodium polyacrylate.

According to a fourth aspect of the present invention there is provided a skin compatible component attachable to mammalian skin manufactured by the method as claimed herein.

According to a further aspect of the present invention there is provided a method of manufacturing an ostomy coupling comprising: applying a polyorganosiloxane derived silicone polymer mix to a moisture and gas permeable support layer; curing the organosiloxane derived silicone polymer at the support layer; attaching an ostomy appliance or ostomy appliance connection to a part of the support layer.

BRIEF DESCRIPTION OF DRAWINGS

A specific implementation of the present invention will now be described, by way of example only, and with reference to the accompanying drawings in which:

FIG. 3 is a plan view of an ostomy appliance coupling according to a further specific implementation of the present invention;

FIG. 4 is a cross sectional view through B-B of the ostomy coupling of FIG. 3;

DETAILED DESCRIPTION OF PREFERRED EMBODIMENT OF THE INVENTION

A silicone polymer based skin compatible component according to the subject invention is particularly adapted for placement on mammalian skin to have a desired adhesion characteristic so as to remain in secure attachment to the skin (as the skin moves) when worn by a person whilst having the desired release characteristics to allow the component to be removed from the skin. The silicone based component is accordingly a hydrophilic humectant configured to absorb moisture into the silicone matrix without detriment to adhesion, cohesive properties and peel characteristics. The subject component enables transmission of moisture vapour through the body of the matrix so as to allow the skin (in contact with the component) to breathe. Accordingly, the present silicone wafer, due in part, to the composition of the silicone matrix is advantageous to balance moisture absorption with moisture and water vapour transmission to avoid skin maceration.

The subject invention is particularly suitable to secure medical appliances or devices to mammalian skin and in particular peri-skin and peristomal skin. Such devices may include but are not limited to catheters, intravenous feeding lines, securement devices, wound dressings, therapeutic devices, drug delivery devices, ostomy appliances and the like.

Figure 2:
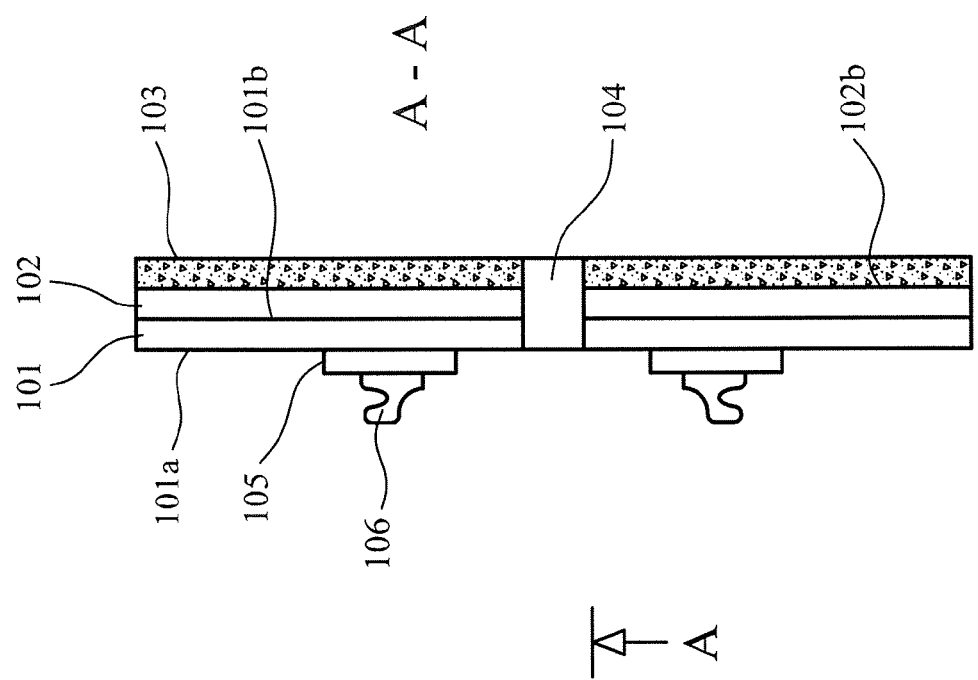
FIG. 2 is a cross sectional view through A-A of the ostomy coupling of FIG. 1.
Figure 1:
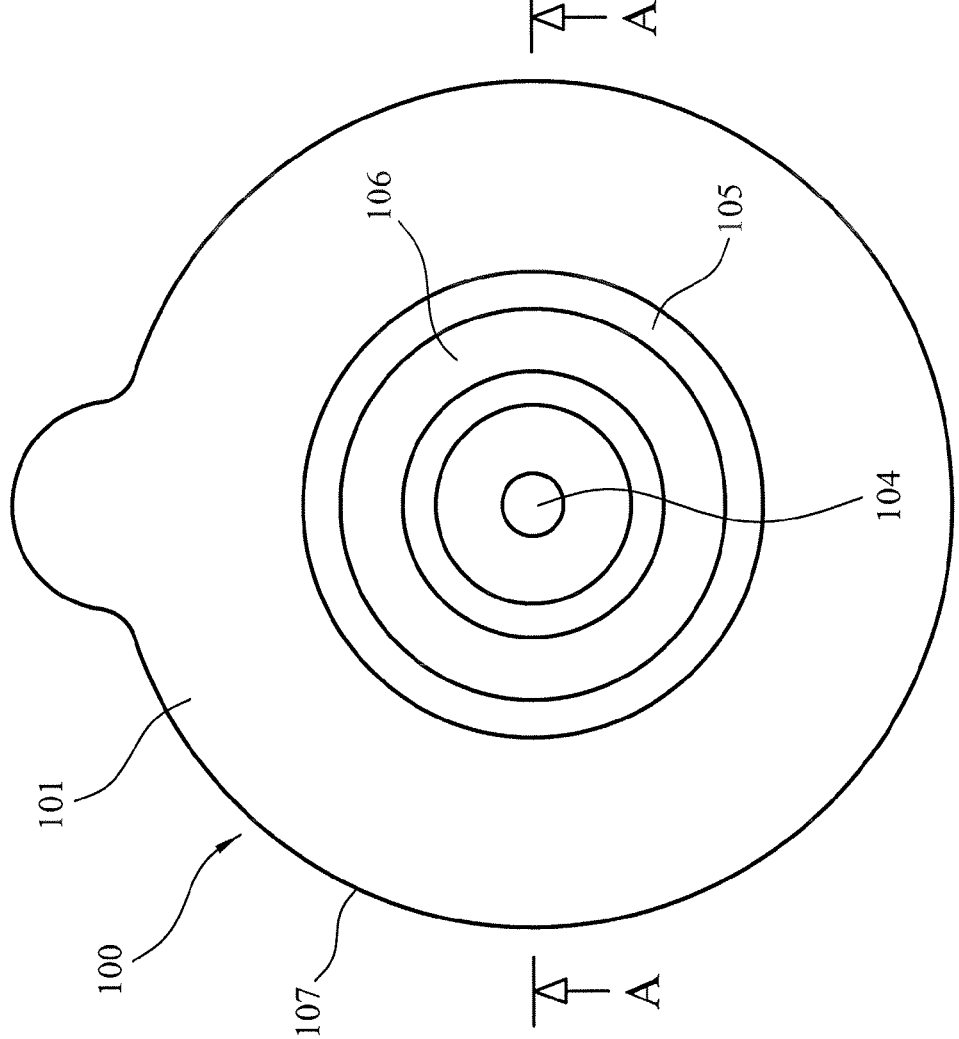
FIG. 1 is a plan view of an ostomy appliance coupling according to a specific implementation of the present invention.

The subject invention will now be described with reference to a specific implementation in which the moisture absorbing particulate silicone based matrix forms a component part of an ostomy appliance coupling referred to as a 'base plate' of a 'two-piece' system. However, the subject invention may be utilised within a 'one-piece' ostomy appliance as will be appreciated. Referring to FIGS. 1 and 2, a coupling assembly 100 comprises a moisture and water vapour permeable 'breathable' substrate layer 101 having a first surface 101a and a second surface 101b. According to the specific implementation, layer 101 comprises a polyurethane having a moisture vapour transmission rate (MVTR) of greater than 700 $g \cdot m^{-2} \cdot 24 \ h^{-1}$ and preferably a MVTR of 700 to 950 $g \cdot m^{-2} \cdot 24 \ h^{-1}$ using an upright cup method. According to the specific implementation, the polyurethane layer has an MVTR of 875 $g \cdot m^{-2} \cdot 24 \ h^{-1}$ using an upright cup method. A polyethylene disc 105 is secured to substrate first layer 101a via RF or ultrasonic welding or using an adhesive. The polyethylene disc 105 provides a mount for a first part 106 of an ostomy appliance coupling mechanism to releasably engage with a second part of the coupling mechanism provided at an ostomy appliance, in particular an ostomy bag. Coupling first part 106 is preferably formed as an annular flange capable of frictionally integrating and releasably locking with the second part of the coupling mechanism so as to provide a sealed coupling between an ostomy bag (not shown) and the coupling arrangement 100 of FIGS. 1 and 2. According to the specific implementation, the first part 106 of the coupling mechanism (being any form of connection as will be appreciated and recognised by those skilled in the art) is secured to layer 105 via RF or ultrasonic welding. However, according to further implementations layer 105 may be a double sided adhesive tape (annular ring) suitable to bond to surface 101a and component part 106.

A silicone polymer matrix layer 102 is applied to substrate second surface 101b by coating second surface 101b with a homogenous liquid phase non-cured silicone polymer mix that is then cured (i.e., room temperature vulcanised) in position at substrate 101. The silicone polymer layer 102 is coated and protected by a release liner 103. Release liner 103 according to the specific implementation comprises a fluoropolymer treated film. Liner 103 is releasably positioned over the silicone layer 102 and is removed prior to mounting of the coupling assembly 100 onto the skin of a person via mating contact with the silicone polymer layer surface 102b.

Layers 101, 102 are annular having a generally circular or oval disc shape profile. A through bore 104 extends through layers 101, 102 and is dimensioned to comprise an internal diameter slightly greater than an external diameter of a stoma with layers 101 and 102 having a generally circular outer perimeter 107 so that the present coupling may be regarded as a generally annular disc. Accordingly, coupling assembly 100 is configured for mounting in close fitting and sealing contact with the peristomal skin as is conventional with both one-piece and two-piece stoma appliances.

According to the specific implementation, polyurethane substrate 101 comprises a layer thickness of 20 μm to 50 μm and the silicone polymer layer 102 comprises a thickness of approximately 400 to 900 μm. Polyethylene disc 105 comprises a thickness of 80 to 150 μm and release liner 103 comprises a thickness in the range 40 to 150 μm.

FIGS. 2 to 4 illustrate an ostomy appliance coupling according to a second embodiment being a variation of the embodiment described with reference to FIGS. 1 to 2. According to the further embodiment, the breathable polyurethane layer 101, the silicone polymer layer 102 and the release liner 103 are as described for the first embodiment. However, in place of the polyethylene disc 105 a weldable non-woven layer 200 is secured to polyurethane first surface 101a. Non-woven layer 200 is also annular and comprises internal and external diameters corresponding to layers 101, 102 so as to form a welded extension of layers 101, 102 in the plane B-B. According to the specific implementation, a thickness of the non-woven layer 200 is 30 to 600 μm. The first part 106 of the appliance coupling mechanism is then welded to non-woven layer 200 via RF or ultrasonic welding.

A specific embodiment of the polymer layer 102 will now be described by reference to the following examples.

Polymer layer 102 is formed as a silicone polymer matrix derived from the addition curing of a first part and a second part. Supplementary components are included within the first and/or second parts to achieve the desired physical and mechanical characteristics of the resulting silicone network in addition to achieving the desired balance of viscoelastic properties, adhesive tack, adhesive peel, moisture absorption, cohesive strength and water vapour transmission rate (WVTR).

The two-part components may be cured/vulcanised at ambient temperatures (or elevated temperatures including in the range 30° to 150°). Curing/vulcanisation times may vary depending upon relative concentrations and components within the first and second parts.

Example 1—MIX #548

TABLE 1 starting materials of liquid phase non-cured mix example 1

| Component | Concentration % w/w | Purpose | Supplier |
|---|---|---|---|
| Silicone Silpuran ® 2122 part A | 33.60 | Part A silicone + catalyst | Wacker Chemie |
| Silicone Silpuran ® 2122 part B | 35.40 | Part B silicone cross-linker | Wacker Chemie |
| Aquakeep ™ Sodium Polyacrylate | 25.00 | Moisture control, moisture transmission through silicone adhesive network | Sumitomo Seika Chemicals Co., Ltd |
| MQ Silanol Resin | 5.00 | Tackifier | Milliken ™ SiVance LLC |
| Aerosil ™ (Fumed silica) | 1.00 | Cohesive strengthener | Evonik Industries AG |

Example 2—MIX #546

TABLE 2 starting materials of liquid phase non-cured mix example 2

| Component | Concentration % w/w | Purpose | Supplier |
|---|---|---|---|
| Silicone Silpuran ® 2122 part A | 31.25 | Part A silicone + catalyst | Wacker Chemie |
| Silicone Silpuran ® 2122 part B | 33.75 | Part B silicone cross-linker | Wacker Chemie |
| Aquakeep ™ Sodium Polyacrylate | 30.00 | Moisture control, moisture transmission through silicone adhesive network | Sumitomo Seika Chemicals Co., Ltd |
| LIR-310 Kurraray | 5.00 | | |

Example 3—MIX #543

TABLE 3 starting materials of liquid phase non-cured mix example 3

| Component | Concentration % w/w | Purpose | Supplier |
|---|---|---|---|
| Silicone Silpuran ® 2122 part A | 38.46 | Part A silicone + catalyst | Wacker Chemie |
| Silicone Silpuran ® 2122 part B | 41.54 | Part B silicone cross-linker | Wacker Chemie |
| Aquakeep ™ Sodium Polyacrylate | 20.00 | Moisture control, moisture transmission through silicone adhesive network | Sumitomo Seika Chemicals Co., Ltd |

Example 4—MIX #535

TABLE 4 starting materials of liquid phase non-cured mix example 4

| Component | Concentration % w/w | Purpose | Supplier |
|---|---|---|---|
| Silicone Silpuran® 2122 part A | 52.40 | Part A silicone + catalyst | Wacker Chemie |
| Silicone Silpuran® 2122 part B | 47.60 | Part B silicone cross-linker | Wacker Chemie |

Example 5—MIX #27

TABLE 5 starting materials of liquid phase non-cured mix example 5

| Component | Concentration % w/w | Purpose | Supplier |
|---|---|---|---|
| Silicone Silpuran® 2130 part A | 45.00 | Part A silicone + catalyst | Wacker Chemie |
| Silicone Silpuran® 2130 part B | 45.00 | Part B silicone cross-linker | Wacker Chemie |
| Aquakeep™ Sodium Polyacrylate | 8.00 | Moisture control, moisture transmission through silicone adhesive network | Sumitomo Seika Chemicals Co., Ltd |
| Aerosil™ (Fumed silica) | 1.00 | Cohesive strengthener | Evonik Industries AG |
| Glycerol | 1.00 | | |

Example 6—MIX #11

TABLE 6 starting materials of liquid phase non-cured mix example 6

| Component | Concentration % w/w | Purpose | Supplier |
|---|---|---|---|
| Silicone Silpuran® 2117/2140 part A | 46.95 | Part A silicone + catalyst | Wacker Chemie |
| Silicone Silpuran® 2117/2140 part B | 46.95 | Part B silicone cross-linker | Wacker Chemie |
| Sodium carboxymethylcellulose Aqualon CMC 7HF PH | 5.00 | | |

TABLE 6-continued starting materials of liquid phase non-cured mix example 6

| Component | Concentration % w/w | Purpose | Supplier |
|---|---|---|---|
| Aerosil™ (Fumed silica) | 0.10 | Cohesive strengthener | Evonik Industries AG |
| Glycerol | 1.00 | | |

Manufacture Method

The Silpuran® based parts A and B were weighed and the other components, of the examples added at their respective concentrations. The components were mixed thoroughly to ensure complete dispersal of the components and in particular the SAP (i.e., sodium polyacrylate) within the mix. This is advantageous to provide a complete heterogeneous dispersion of the components and in particular the complete distribution of the moisture absorbing particulate (SAP) within the silicone matrix. In particular, thorough mixing reduces the risk of the SAPs agglomerating which would be detrimental to the moisture management characteristics across the full surface area of the skin compatible component. The above components were mixed using a medium to low shear mixing technique either by centrifusion or dispersal at 1000 to 3000 rpm. Surplus heat energy was removed by active cooling. Vacuum phase mixing was used as a final stage to provide a liquid phase non-cured silicone formulation. The laminate assembly 100 of FIGS. 1 to 4 was manufactured by layering the liquid phase silicone formulation onto the polyurethane layer surface 101b followed by room temperate vulcanisation (RTV) under controlled conditions. The release liner 103, the polyethylene disc 105 and the coupling first part 106 was then attached to form the multi component assembly 100.

Performance and Results

The present silicone adhesive is advantageous to provide a 'soft' atraumatic release from the skin so as to reduce the potential for skin stripping/damage. Additionally, the present adhesive comprises the desired cohesive strength and tack adhesion so as to be maintained in position for extended wear times of the order of over 400 hours without degradation and loss of moisture absorption and transmission at the adhesive layer. The present invention provides a balance of wear performance characteristics for skin compatibility including in particular edge lift, adhesion during wear, adhesion on removal, moisture control, skin condition after wear, skin trauma on removal and skin residue on removal. The present silicone adhesive is advantageous so as to be capable of being worn continuously during low, modest and high physical activity levels and movement as a wearer engages in such physical activity. The present skin adhesive is further advantageous to satisfy other ergonomic factors such as comfort during wear and conformity to skin/body topography.

To assess the wear performance characteristics, a series of wear tests were undertaken using the above examples 1 to 7. All wear tests were untaken on a male, in the age range 51-60.

TABLE 8

Standard Hydrocolloid Adhesives (control)

| Formulation # | Form | Wear time (h) | Edge lift during wear | Adhesion during wear | Adhesion on removal | Moisture under adhesive | Skin condition on removal | Trauma on removal | Residue on removal | Coating Substrate |
|---|---|---|---|---|---|---|---|---|---|---|
| 90 mins Cardio-vascular activity/1 × shower | | | | | | | | | | |
| Control - CP Sensura 10021 | Wafer | 72 | Low Some creasing | Feels secure | Very high | None | Healthy | High Some reddening | None | PE base plate |

TABLE 8-continued

Standard Hydrocolloid Adhesives (control)

| Formulation # | Form | Wear time (h) | Edge lift during wear | Adhesion during wear | Adhesion on removal | Moisture under adhesive | Skin condition on removal | Trauma on removal | Residue on removal | Coating Substrate |
|---|---|---|---|---|---|---|---|---|---|---|
| Base plate | | | due to stiffness of coated substrate | | | | | caused by trauma. Very tight on removal | | |
| 60 mins Cardio-vascular activity/4 × showers | | | | | | | | | | |
| Control - CP Sensura 10021 Base plate | Wafer | 98 | High Significant edge lift on top side of outer diameter | Feels secure | High | None | Dry | High Very uncomfortable. Skin reddening due to trauma of removal. | Slight Slight residues at edges of wafer | PE base plate |

TABLE 9

Co-polyester Film substrate - PT RTV Cure Silicone (2)

| Formulation # | Form | Wear time (h) | Edge lift during wear | Adhesion during wear | Adhesion on removal | Moisture under adhesive | Skin condition on removal | Trauma on removal | Residue on removal | Coating Substrate |
|---|---|---|---|---|---|---|---|---|---|---|
| Normal activity - recorded as fail due to edge lift & channels with this formulation & coating substrate. | | | | | | | | | | |
| High levels of creasing leading to channels for leak with this substrate | | | | | | | | | | |
| 11 (2117/2140) | Wafer | 74 | High | Does not feel secure | High | None | Healthy | Acceptable | | Co-polyester Film |

TABLE 10

PU/Polyester Non-woven - 2PT RTV Cure Silicone (1)

| Formulation # | Form | Wear time (h) | Edge lift during wear | Adhesion during wear | Adhesion on removal | Moisture under adhesive | Skin condition on removal | Trauma on removal | Residue on removal | Coating Substrate |
|---|---|---|---|---|---|---|---|---|---|---|
| Normal activity - recorded as fail due to edge lift and channels. Overall adhesion needs to be increased | | | | | | | | | | |
| Uncomfortable in wear. Substrate causes creases and channels leading to edge lift. Substrate has insufficient elasticity. | | | | | | | | | | |
| 27 (2130) | Wafer | 39 | Medium | Feels secure | Medium | None | Healthy | None | None | PU/Polyester non-woven |
| Normal activity - recorded as fail due to edge lift and channels. Overall adhesion needs to be increased | | | | | | | | | | |
| Wafer fell off when showering. Lots of wrinkling. | | | | | | | | | | |
| 27 (2130) | Wafer | 66 | Low | Feels secure | Medium | Not determined | Moist | None | None | PU/Polyester non-woven |
| Normal activity - 6× showers. Coating substrate leads to some wrinkling during wear. Overall adhesion needs to increase to improve security. | | | | | | | | | | |
| 27 (2130) | Wafer | 144 | None | Feels secure | High | None | Healthy | None | None | PU/Polyester non-woven |
| Normal activity - Only short wear time achieved. Failure caused by creasing. Sub optimal film substrate. Overall adhesion needs to increase. | | | | | | | | | | |
| 27 (2130) | Wafer | 29 | None | Feels secure | Fails Creasing | None | Healthy | None | Acceptable | PU/Polyester non-woven |
| Normal activity - Adhesive cohesion needs to be improved. Overall adhesion needs to increase. | | | | | | | | | | |
| Poor cohesion of silicone gel to coating substrate causes edge lift and slight residues | | | | | | | | | | |
| 27 (2130) | Wafer with bag in-situ. 200 g load | 86 | Medium | Feels secure | High | None | Healthy | None | Slight | PU/Polyester non-woven |

TABLE 10-continued

PU/Polyester Non-woven - 2PT RTV Cure Silicone (1)

| Formulation # | Form | Wear time (h) | Edge lift during wear | Adhesion during wear | Adhesion on removal | Moisture under adhesive | Skin condition on removal | Trauma on removal | Residue on removal | Coating Substrate |
|---|---|---|---|---|---|---|---|---|---|---|
| Normal activity - Adhesive cohesion needs to be improved. Some skin chafing occurred where ring sits. Overall adhesion needs to increase. | | | | | | | | | | |
| Poor cohesion of silicone gel to coating substrate causes edge lift and slight residues | | | | | | | | | | |
| 27 (2130) | Wafer with bag in-situ. 200 g load | 76 | Medium | Feels secure | High | None | Slight reddening | None | None | PU/Polyester non-woven |

TABLE 11

PU Film - 2PT RTV Cure Silicone (2)

| Formulation # | Form | Wear time (h) | Edge lift during wear | Adhesion during wear | Adhesion on removal | Moisture under adhesive | Skin condition on removal | Trauma on removal | Residue on removal | Coating Substrate |
|---|---|---|---|---|---|---|---|---|---|---|
| Normal activity - recorded as fail due to edge lift. Formulation prone to leaving skin residues. | | | | | | | | | | |
| 11 (2117/2140) | Wafer | 74 | Low | Feels secure | High | None | Healthy | Acceptable | None | PU Film |
| Normal activity - recorded as fail due to edge lift. | | | | | | | | | | |
| 11 (2117/2140) | Wafer | 74 | Low | Feels secure | High | None | Healthy | None | None | PU Film |

TABLE 12

PU Film - 2PT RTV Cure Silicone (3) - Ratio Adjustment

| Formulation # | Form | Wear time (h) | Edge lift during wear | Adhesion during wear | Adhesion on removal | Moisture under adhesive | Skin condition on removal | Trauma on removal | Residue on removal | Coating Substrate |
|---|---|---|---|---|---|---|---|---|---|---|
| Normal activity - Recorded as fail due to edge lift | | | | | | | | | | |
| 546 (2122) | Strip | 48 | Some edge lift | Feels secure | High | None | Healthy | None | None | PU Film |
| Normal activity - Recorded as fail due to edge lift | | | | | | | | | | |
| 543 (2122) | Strip | 24 | Some edge lift | Feels secure | High | None | Healthy | None | None | PU Film |
| Normal activity - recorded as fail due to excess adhesion/tack & poor handleability | | | | | | | | | | |
| Very tacky with poor anchorage to film substrate. Silicone rubs off to form residues. Handling of wafer problematic. | | | | | | | | | | |
| 535 (2122) | Strip | 24 | Excessive adhesion & Tack | Feels secure | High | None | Healthy | Removal problematic | High | PU Film |

TABLE 13

PU Film - 2PT RTV Cure Silicone (3) Optimisation

| Formulation # | Form | Wear time (h) | Edge lift during wear | Adhesion during wear | Adhesion on removal | Moisture under adhesive | Skin condition on removal | Trauma on removal | Residue on removal | Coating Substrate |
|---|---|---|---|---|---|---|---|---|---|---|
| Normal activity/3 × showers | | | | | | | | | | |
| 548 (2122) - Best Performing | Wafer with bag in-situ. 200 g | 72 | None | Feels secure | High | None | Healthy | Low Low - acceptable | None | PU Film |

TABLE 13-continued

PU Film - 2PT RTV Cure Silicone (3) Optimisation

| Formulation # | Form | Wear time (h) | Edge lift during wear | Adhesion during wear | Adhesion on removal | Moisture under adhesive | Skin condition on removal | Trauma on removal | Residue on removal | Coating Substrate |
|---|---|---|---|---|---|---|---|---|---|---|
| 180 mins Cardio-vascular activity/Swimming - Badminton - Sauna & Steam room | | | | | | | | | | |
| 548 (2122) - Best Performing | Wafer | 163 | Acceptable V. Minor edge lift at the top outer diameter after 5 day of wear | Feels secure Very secure | High | None | Healthy | Acceptable | Acceptable | PU Film |
| Normal activity | | | | | | | | | | |
| 548 (2122) - Best Performing | Wafer | 144 | Acceptable V. Minor edge lift. | Feels secure | High | None | Healthy | None | None | PU Film |
| 548 (2122) - Best Performing | Strip | 96 | Acceptable | Feels secure | High | None | Healthy | Acceptable | Acceptable | PU Film |
| Normal activity | | | | | | | | | | |
| 548 (2122) - Best Performing | Strip | 144 | Acceptable | Feels secure | High | None | Healthy | Acceptable | Acceptable No residues | PU Film |
| Normal activity | | | | | | | | | | |
| 548 (2122) - Best Performing | Strip | 432 | Acceptable V. Minor edge lift after 18 days wear. | Feels secure Excellent adhesion | High | None | Healthy | Acceptable | Acceptable | PU Film |

Comments referring to table 8—Wear tests highlight the shortcomings of the standard skin covering adhesive particularly in terms of trauma on removal and edge lift caused by the stiff base plate material.

Comments referring to table 9—Change of coating substrate to co-polyester film and silicone formulation did not improve wear performance in terms of edge lift and security during wear time.

Comments referring to table 10—Introduction of a PU/polyester non-woven coating substrate gives some overall improvement in the wear performance characteristics. Edge lift and adhesion are of concern and the overall strength of adhesion needs was considered not optimised.

Comments referring to table 11—Change to silicone polymer formulation and coating substrate give further improvement. Further improvement required due to reduce edge lift and to reduce residues on removal.

Comments referring to table 12—PU film coating substrates presenting best comfort and conformability. Change to higher adhesion silicone polymer formulation to improve overall adhesion and security during wear time.

Mix #535 demonstrated desired tack and adhesion but poor handling and removal. Tack and adhesion were considered too high and formulation refinement was considered required. Mix #543 demonstrated reduced adhesion and tack resulting in edge lift. Mix #546 due to addition of tackifier at 5 wt % and super-absorbent polymer at 30 wt %, still demonstrated some edge lift.

Comments referring to table 13—PU film provides excellent comfort and conformability in wear. The silicone formulation Mix #548 provides optimises tack/adhesion, security during wear and the other associated wear performance characteristics. Mix #548 (Example 1) provides the desired performance across all attributes and offers wear times in excess of 70 hours and potentially up to or beyond 400 hours continuous attachment.

Figure 5A:
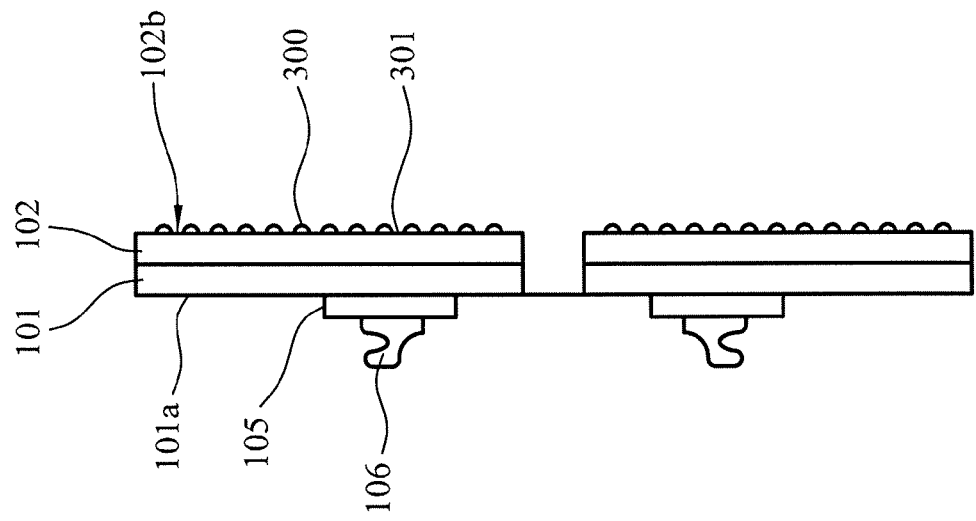
FIG. 5A is a cross section through an ostomy coupling of the type of FIGS. 1 and 2 according to a further embodiment having an additional adhesive layer at the skin contact face of the coupling that is discontinuous over the skin contact face.
Figure 5B:
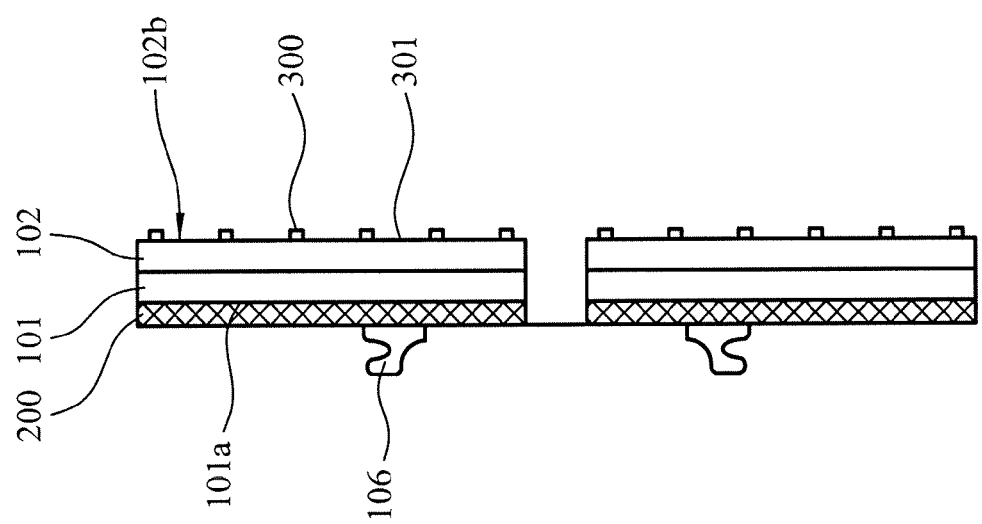
FIG. 5B is a cross section through an ostomy coupling of the type of FIGS. 3 and 4 according to a further embodiment having an additional adhesive layer at the skin contact face of the coupling that is discontinuous over the skin contact face.

Further embodiments of the present invention are illustrated referring to FIGS. 5A and 5B, with FIG. 5A being a variation of the embodiment of FIGS. 1 and 2 and FIG. 5B being a variation of the embodiment of FIGS. 3 and 4. According to both further embodiments, an additional skin contact layer 300 is adhered to and positioned at surface 102b of silicone polymer matrix layer 102. The additional skin contact layer 300 is preferably formed from the same material as layer 102. However, different materials may be used such as silicones or hydrocolloid based materials.

The additional skin contact layer 300 may be regarded as an additional adhesive layer formed from narrow ridges that are discontinuous over surface 102b such that additional skin contact layer 300 does not coat completely the surface 102b and there is provided regions 301 that are devoid of additional skin contact layer 300 with regions 301 being exposed surface areas of the silicone polymer matrix layer 102.

According to embodiments of FIG. 5A the pattern of the additional skin contact layer 300 at surface 102b is a rectangular grid pattern or concentric circles formed by uniform ridges extending across surface 102b. The spaces between the ridges may be equal in the respective directions across surface 102b.

The embodiment of FIG. 5B comprises the additional skin contact layer 300 formed as a regular repeating array of nodes or bumps. The bumps may be separated from one another by a regular or uniform discreet separation distance such that the skin contact surface 102b of the silicone polymer matrix layer 102 is exposed at spacings 301 between the bumps 300.

According to a specific embodiment the additional skin contact layer 300 at surface 102b is formed as a series of concentric circles extending radially between central bore 104 and outer perimeter 107. The concentric circles (or other polygonal (i.e., rectangular) or non-polygonal (i.e., oval) shapes) may be spaced apart from one another in the radial direction to be formed as discreet ridges separated by regions of exposed surface 102b. Such an embodiment is further beneficial to increase the strength and integrity of the moisture seal of the present coupling and reduce the risk of fluid leakage from under the coupling between the surface 102b and the skin.

The invention claimed is:

1. A skin compatible component attachable to mammalian skin comprising:
a silicone polymer network derived from addition curing of a first part including a vinyl functionalised siloxane polymer and a second part including a silicon hydride containing crosslinker, in the presence of a metal catalyst; and
a superabsorbent particulate distributed within the polymer network at a concentration in a range of 5 to 45 wt % and having an average particle size in a range of 10 to 40 μm, the superabsorbent particulate configured to absorb moisture from the skin,
wherein the first part or the second part includes a MQ resin, and the first part or the second part includes fumed silica.

2. The component as claimed in claim 1, wherein the average particle size of the superabsorbent particulate is in a range of 15 to 35 μm or 20 to 30 μm.

3. The component as claimed in claim 1, wherein the superabsorbent particulate is distributed within the polymer network at a concentration in a range of 10 to 40 wt %, 15 to 35 wt % or 20 to 30 wt %.

4. The component as claimed in claim 1, wherein the superabsorbent particulate comprises any one or a combination of the set of:
a naturally occurring hydrocolloid;
a semi-synthetic hydrocolloid; or
a synthetic hydrocolloid.

5. The component as claimed in claim 1, wherein the superabsorbent particulate comprises any one or a combination of:
a polysaccharide;
a cellulose;
hydroxyethylcellulose;
carboxymethylcellulose;
hydroxypropylcellulose.

6. The component as claimed in claim 1, wherein the superabsorbent particulate comprises any one or a combination of:
carboxymethyl β-glucan;
cross-linked sodium carboxymethyl cellulose;
sodium carboxymethyl cellulose; or
methylcellulose.

7. The component as claimed in claim 1, wherein the superabsorbent particulate comprises sodium polyacrylate.

8. A method of manufacturing a skin compatible component attachable to mammalian skin comprising:
mixing a first part including a vinyl functionalized siloxane polymer with a second part including a silicon hydride containing crosslinker to form a mix, the first part or the second part including an MQ resin, and the first part or the second part including fumed silica;
incorporating within the mix a superabsorbent particulate having an average particle size in a range 10 to 40 μm; and
addition curing the mix via a metal catalyst to form a silicone polymer network,
wherein the superabsorbent particulate is distributed within the silicone polymer network at a concentration in a range of 5 to 45 wt %.

9. The method as claimed in claim 8, wherein the superabsorbent particulate comprises any one or a combination of the set of:

a naturally occurring hydrocolloid;
a semi-synthetic hydrocolloid; or
a synthetic hydrocolloid.

10. The method as claimed in claim 8, wherein the superabsorbent particulate comprises any one or a combination of:
a polysaccharide;
a cellulose;
hydroxyethylcellulose;
carboxymethylcellulose;
hydroxypropylcellulose.

11. The method as claimed in claim 8, wherein the superabsorbent particulate comprises any one or a combination of:
carboxymethyl β-glucan;
cross-linked sodium carboxymethyl cellulose;
sodium carboxymethyl cellulose; or
methylcellulose.

12. The method as claimed in claim 8, wherein the superabsorbent particulate comprises sodium polyacrylate.

13. The method as claimed in claim 8, wherein the MQ resin is included in the mix at 2 to 8 wt % or 3 to 7 wt %.

14. The method as claimed in claim 8, wherein the fumed silica comprises a bulk density of 0.4 to 0.8 g/mL and a Brunauer-Emmitt-Teller (BET) specific surface area of 200 to 320 $mm^2/g$, 210 to 310 $mm^2/g$, 230 to 300 $mm^2/g$ or 230 to 290 $mm^2/g$.

15. The method as claimed in claim 8, wherein the fumed silica is included within the mix at 0.2 to 2.0 wt %, 0.3 to 2.0 wt %, 0.5 to 1.5 wt % or 0.8 to 1.2 wt %.

16. The method as claimed in claim 8, wherein the average particle size of the superabsorbent particulate is in a range of 15 to 35 μm or 20 to 30 μm.

17. The method as claimed in claim 16, wherein the superabsorbent particulate is included within the mix at 15 to 35 wt % or 20 to 30 wt %.

18. The method as claimed in claim 8, wherein the superabsorbent particulate comprises any one or a combination of the set of:
a naturally occurring hydrocolloid;
a semi-synthetic hydrocolloid; or
a synthetic hydrocolloid.

19. The method as claimed in claim 8, wherein the superabsorbent particulate comprises any one or a combination of:
a polysaccharide;
a cellulose;
hydroxyethylcellulose;
carboxymethylcellulose;
hydroxypropylcellulose.

20. The method as claimed in claim 8, wherein the superabsorbent particulate comprises any one or a combination of:
carboxymethyl β-glucan;
cross-linked sodium carboxymethyl cellulose;
sodium carboxymethyl cellulose; or
methylcellulose.

21. The method as claimed in claim 8, wherein the superabsorbent particulate comprises sodium polyacrylate.

22. The method as claimed in claim 8, wherein the vinyl functionalized siloxane polymer comprises a vinyl-terminated polydimethylsiloxane (PDMS).

23. The method as claimed in claim 8, wherein the silicon hydride containing crosslinker comprises a hydride-terminated polydimethylsiloxane (PDMS).

24. The method as claimed in claim 23, wherein the vinyl-terminated polydimethylsiloxane (PDMS) comprises a first vinyl-terminated PDMS having a mass average of 10,000 to 20,000 and a second vinyl-terminated PDMS having a mass average of 70, 000 to 100,000.

25. The method as claimed in claim 8, wherein the vinyl functionalized siloxane polymer comprises a vinyl-terminated polydimethylsiloxane (PDMS) and the silicon hydride containing crosslinker comprises a hydride-terminated polydimethylsiloxane (PDMS).

26. The method as claimed in claim 25, wherein the first part is included within the mix at 30 to 40 wt % or 31 to 35 wt % and the second part is included within the mix at 30 to 40 wt % or 33 to 37 wt %.

27. The method as claimed in claim 26, wherein the superabsorbent particulate is included within the mix at 20 to 30 wt % or 22 to 28 wt %.

28. The method as claimed in claim 27, wherein the MQ resin is included in the mix at 2 to 8 wt % or 3 to 7 wt %.

29. The method as claimed in claim 28, wherein the fumed silica is included within the mix at 0.2 to 2.0 wt %, 0.5 to 1.5 wt % or 0.8 to 1.2 wt %.

30. The method as claimed in claim 29, wherein the first part further comprises an organoplatinum catalyst and a silicone-vinyl containing inhibitor and the second part further comprises a vinyl-terminated polydimethylsiloxane (PDMS) and wherein the superabsorbant particulate is sodium polyacrylate.

31. A skin compatible component attachable to mammalian skin manufactured by the method of claim 8.

* * * * *